United States Patent [19]

Graf

[11] 4,377,696

[45] Mar. 22, 1983

[54] PREPARATION OF 4-METHYLIMIDAZOLES

[75] Inventor: Fritz Graf, Speyer, Fed. Rep. of Germany

[73] Assignee: BASF Aktiengesellschaft, Ludwigshafen, Fed. Rep. of Germany

[21] Appl. No.: 253,805

[22] Filed: Apr. 13, 1981

[30]     Foreign Application Priority Data

May 14, 1980 [DE]   Fed. Rep. of Germany ....... 3018458

[51] Int. Cl.³ ........................................... C07D 233/58
[52] U.S. Cl. .................................................... 548/335
[58] Field of Search ......................................... 548/335

[56]            References Cited

U.S. PATENT DOCUMENTS 3,715,365  2/1973  Schulze ............................... 548/335
4,074,054  2/1978  Christidis et al. ................... 548/335

FOREIGN PATENT DOCUMENTS 58122  9/1969  Poland .
51788  7/1969  Romania .

OTHER PUBLICATIONS

Sasaki, Chem. Abst. 1959, vol. 53, p. 11392a.

*Primary Examiner*—Henry R. Jiles
*Assistant Examiner*—Natalia Harkaway
*Attorney, Agent, or Firm*—John H. Shurtleff

[57]            ABSTRACT

A process for the preparation of 4-methylimidazoles by reacting methylglyoxal with ammonia and an aldehyde in aqueous solution, wherein the reaction is carried out at a pH of above 7 and either the reactants are all brought into contact simultaneously or the aldehyde and the methylglyoxal are added simultaneously to the aqueous ammonia solution.

5 Claims, No Drawings

PREPARATION OF 4-METHYLIMIDAZOLES

The present invention relates to a process for the preparation of 4-methylimidazoles.

4-Methylimidazole may be prepared, for example, by catalytically cyclizing propylene-1,2-diamine and formic acid to give 4-methylimidazoline from which hydrogen is then eliminated. 4-Methylimidazole has also been prepared by reacting methylglyoxal or methylglyoxal-dimethylacetal with formaldehyde in an aqueous medium in the presence of an ammonium salt of a strong acid.

In this latter process, disclosed in U.S. Pat. No. 3,715,365, the reaction is carried out at a pH of 7 or below. This process presents corrosion problems when carried out industrially, and also necessitates handling large amounts of inorganic salt solutions.

I have found that 4-methylimidazoles can be prepared particularly advantageously by reacting methylglyoxal with ammonia and an aldehyde in aqueous solution, if the reaction is carried out at a pH of above 7 and either the reactants are all brought into contact simultaneously or the aldehyde and the methylglyoxal are added simultaneously to the aqueous ammonia solution.

Using the novel process, the 4-methylimidazole is obtained in a yield of up to 80%. This advantageous result was unexpected in view of the statements in U.S. Pat. No. 3,715,365 and in Chem. Abstr. 53 (1959), 11392a, which state that methylglyoxal and ammonia form little or no imidazole.

The novel process can be carried out not only with formaldehyde but also with other aldehydes, for example acetaldehyde, propionaldehyde and benzaldehyde. In that case, the corresponding 2-substituted imidazole is obtained.

The reaction can be carried out at up to 150° C. but is advantageously carried out at from 20° to 100° C. The pH in the reaction mixture must be greater than 7 and is preferably greater than 8, especially 9 or above. The reactants may, for example, be employed in stoichiometric amounts, ie. in a molar ratio of methylglyoxal:aldehyde:ammonia = 1:1:2. Excess ammonia is not a disadvantage. Excess aldehyde, for example up to 100% above the stoichiometric amount, can be advantageous, since it suppresses the formation of 2,4-dimethylimidazole. The sequence of addition of the reactants is of great importance. For example, if the aqueous ammonia is added to the aldehydes, unsatisfactory yields are obtained.

The 4-methylimidazoles obtainable by the novel process are valuable intermediates, for example for the preparation of drugs.

In the Examples, parts and percentages are by weight.

EXAMPLE 1

A mixture of 112 parts of a 32.4% strength aqueous methylglyoxal solution and 37.5 parts of a 40% strength aqueous formaldehyde solution is added dropwise simultaneously with 102 parts of 25% strength aqueous ammonia, to 1,350 parts of water, in the course of 30 minutes, whilst stirring and cooling to give a temperature of 40° C. in the reaction mixture. The pH of the reaction mixture is from 9.2 to 9.4 at the beginning of the addition and remains above 9 throughout the reaction. After all has been added, stirring is continued for about 30 minutes at 40° C. and the mixture is then extracted with 4×500 parts of isobutanol. The combined isobutanol extracts are worked up by distillation. 30.7 parts of 4-methylimidazole (boiling point 144°–147° C./1 mm Hg, melting point 49° C.) are obtained, corresponding to a yield of 74.9% of theory, based on methylglyoxal employed.

EXAMPLE 2

A mixture of 456 parts of a 15.8% strength aqueous methylglyoxal solution and 75 parts of a 40% strength formaldehyde solution is added dropwise, in the course of 30 minutes, to 999 parts of a 5.1% strength aqueous ammonia solution at 70° C., with thorough stirring. The pH in the reaction mixture remains above 9 throughout the reaction. After all has been added, stirring is continued for about 30 minutes. The mixture is then extracted with isobutanol and the extracts are worked up by distillation. 65.2 parts of 4-methylimidazole are obtained, corresponding to 79.2%, based on methylglyoxal employed.

EXAMPLE 3

89 parts of a 32.4% strength aqueous methylglyoxal solution are mixed with 36 parts of acetaldehyde and this mixture is added dropwise, simultaneously with 82 parts of 25% strength aqueous ammonia solution, to 850 parts of water at 40° C. in the course of 30 minutes, whilst stirring. The pH of the reaction mixture is 9.2–9.4 at the start of the addition and remains above 9 throughout the reaction. After all has been added, the mixture is stirred for a further 30 minutes at 40° C. It is then worked up by distillation. 23.6 parts of 2,4-dimethylimidazole (boiling point 140°–143° C./1 mm Hg) are obtained, corresponding to a yield of 72.0%.

EXAMPLE 4 (COMPARATIVE EXAMPLE)

102 parts of 25% strength aqueous ammonia are added, in the course of 30 minutes, to a solution of 112 parts of 32.2% strength aqueous methylglyoxal and 37.5 parts of aqueous 40% strength formaldehyde in 1,275 parts of water at 70° C., whilst stirring. Stirring is then continued for 30 minutes at 70° C., after which the mixture is worked up by distillation. 40.5 parts of 4-methylimidazole are obtained, corresponding to a yield of 49.4%, based on methylglyoxal employed.

I claim:

1. A process for the preparation of a 4-methylimidazole which comprises reacting methylglyoxal with ammonia and an aldehyde in aqueous solution, the reaction being carried out at a pH above 7 and all the reactants being brought into contact simultaneously in an aqueous ammonia reaction solution, with the proviso that the aldehyde and the methylglyoxal may be added separately or together for simultaneous contact with the aqueous ammonia solution.

2. A process as claimed in claim 1, wherein the reaction is carried out at a pH above 8.

3. A process as claimed in claims 1 or 2 wherein the aldehyde is selected from the group consisting of formaldehyde, acetaldehyde, propionaldehyde and benzaldehyde.

4. A process as claimed in claims 1 or 2 wherein the aldehyde is formaldehyde.

5. A process as claimed in claims 1 or 2 wherein the aldehyde is acetaldehyde.

* * * * *